(12) United States Patent
Bigi et al.

(10) Patent No.: US 11,033,890 B2
(45) Date of Patent: Jun. 15, 2021

(54) PROCESSES FOR RECOVERY OF RHODIUM FROM A HYDROFORMYLATION PROCESS

(71) Applicant: Dow Technology Investments LLC, Midland, MI (US)

(72) Inventors: Marinus A. Bigi, Pearland, TX (US); Rick B. Watson, Missouri City, TX (US)

(73) Assignee: DOW TECHNOLOGY INVESTMENTS LLC, Midland, MI (US)

(*) Notice: Subject to any disclaimer, the term of this patent is extended or adjusted under 35 U.S.C. 154(b) by 0 days.

(21) Appl. No.: 16/638,420

(22) PCT Filed: Nov. 2, 2018

(86) PCT No.: PCT/US2018/058904
§ 371 (c)(1),
(2) Date: Feb. 11, 2020

(87) PCT Pub. No.: WO2019/094290
PCT Pub. Date: May 16, 2019

(65) Prior Publication Data
US 2020/0269226 A1    Aug. 27, 2020

Related U.S. Application Data

(60) Provisional application No. 62/585,084, filed on Nov. 13, 2017.

(51) Int. Cl.
| C07C 45/50 | (2006.01) |
| B01J 31/00 | (2006.01) |
| B01J 38/00 | (2006.01) |
| B01J 31/40 | (2006.01) |
| B01J 31/18 | (2006.01) |
| B01J 38/02 | (2006.01) |
| B01J 38/58 | (2006.01) |

(52) U.S. Cl.
CPC ......... B01J 31/4046 (2013.01); B01J 31/185 (2013.01); B01J 38/02 (2013.01); B01J 38/58 (2013.01); C07C 45/50 (2013.01); *B01J 2231/321* (2013.01)

(58) Field of Classification Search
CPC ..... C07C 45/50; B01J 31/4046; B01J 31/185; B01J 38/58
See application file for complete search history.

(56) References Cited

U.S. PATENT DOCUMENTS

| 3,968,134 A | 7/1976 | Gregorio et al. |
| 4,135,911 A | 1/1979 | Balmat |
| 4,148,830 A | 4/1979 | Pruett et al. |
| 4,221,743 A | 9/1980 | Halstead et al. |
| 4,247,486 A | 1/1981 | Brewester et al. |
| 4,341,741 A | 7/1982 | Davidson et al. |
| 4,473,655 A | 9/1984 | Tsunoda et al. |
| 4,504,588 A | 3/1985 | Gartner et al. |
| 4,774,361 A | 9/1988 | Maher et al. |
| 5,681,473 A | 10/1997 | Miller et al. |
| 5,936,130 A | 8/1999 | Mori et al. |
| 6,946,580 B2 | 9/2005 | Banister et al. |
| 7,232,931 B2 | 6/2007 | Toetsch et al. |
| 2003/0018210 A1 | 1/2003 | Gelling et al. |
| 2012/0035382 A1 | 2/2012 | Priske et al. |

FOREIGN PATENT DOCUMENTS

| CN | 1273278 C | 9/2006 |
| CN | 102373335 A | 3/2012 |
| CN | 102557155 B | 7/2013 |
| CN | 102925713 B | 11/2013 |
| CN | 102925699 B | 1/2014 |
| DE | 3235029 A1 | 3/1984 |
| DE | 3347406 A1 | 7/1985 |
| EP | 0829300 A1 | 3/1998 |
| JP | 4548103 B2 | 9/2010 |
| JP | 5665947 B2 | 2/2015 |
| WO | 9003841 A1 | 4/1990 |
| WO | 2017019259 A1 | 2/2017 |

OTHER PUBLICATIONS

Van Leeuwen, Peit. EDS. "Rhodium Catalyzed Hydroformylation," Academic Pub. Chapters 3, 8 and 9 2000.
E.J. Dufek et al., Recovery of Solubilized Rhodium, Journal of the American Oil Chemists, 1977, p. 276-278, vol. 54.
PCT/US2018/058904, International Search Report and Written Opinion dated Jan. 25, 2019.
PCT/US2018/058904, International Preliminary Report on Patentability dated May 19, 2020.

*Primary Examiner* — Sikarl A Witherspoon

(57) ABSTRACT

Some embodiments of the present invention relate to processes to recover rhodium from a hydroformylation process. In some embodiments, the process to recover rhodium from the hydroformylation process comprises (a) treating a catalyst-containing stream from the hydroformylation process with 2.5 to 20 weight percent, based on the total weight of the stream, of a water-soluble organic amine of the following structure: wherein $R^{32}$, $R^{33}$, and $R^{34}$ are each independently alkyls and ethoxylates, and wherein no more than one of $R^{32}$, $R^{33}$, and $R^{34}$ is alkyl; (b) heating the resulting solution in the presence of syngas to a temperature of at least 65° C. to generate a rhodium-rich phase and a supernatant; and (c) removing the supernatant to recover the rhodium-rich phase.

(I)

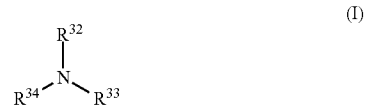

11 Claims, No Drawings

PROCESSES FOR RECOVERY OF RHODIUM FROM A HYDROFORMYLATION PROCESS

FIELD

The present invention relates to processes for recovering rhodium from a hydroformylation process, and in particular, to processes for recovering rhodium from a hydroformylation process wherein the hydroformylation process comprises producing at least one aldehyde in a reaction zone, the reaction zone comprising a $C_7$ to $C_{22}$ olefin, hydrogen, and carbon monoxide in the presence of a catalyst, wherein the catalyst comprises rhodium and an organophosphorus ligand.

BACKGROUND

It is well known that continuous hydroformylation processes will slowly form relatively high-boiling aldehyde-derived byproducts over time (see, e.g., U.S. Pat. Nos. 4,148,830 and 4,247,486). Because these "heavies" (as defined further below) often serve as the reaction solvent, they are initially allowed to accumulate in liquid recycle processes, but adjustments in product separation conditions (e.g., temperature, pressure, strip gas flow rate, etc.) must be made to prevent their concentration from increasing beyond practical limits. Establishing a ratio of reactor effluent (feed) introduced to the separation zone relative to the non-volatiles returned to the reaction zone (tails), while still maintaining the desired aldehyde production rate, will ultimately determine the maximum concentration of heavies that the system may sustain. Once the heavies concentration limit is reached, they must be removed at a rate comparable to their formation rate to maintain the desired balance. One common method of heavies removal is volatilization; however, if the byproducts in question are too high-boiling to distill overhead (e.g., derived from higher olefins), it may be necessary to remove them from the system as a liquid purge stream (e.g. removal of separation zone liquid effluent) to extend catalyst life. Costs are associated with the liquid purge, including in the recovery of rhodium from the liquid purge.

Hydroformylation catalysts comprising rhodium and ligands such as organomonophosphites are capable of very high reaction rates (see, e.g., "Rhodium Catalyzed Hydroformylation," van Leeuwen, Claver, Kluwer Academic Pub. (2000)). Such catalysts have industrial utility, as they can be used to increase production rates, or to efficiently hydroformylate internal and/or branched internal olefins, which react more slowly than linear alpha olefins.

Accordingly, a number of processes have been developed to remove and recover rhodium from streams in hydroformylation processes such as liquid purge streams with heavies. It would be desirable to have alternative processes for recovering rhodium from hydroformylation processes, particularly in the hydroformylation of higher olefins.

SUMMARY

It has surprisingly been discovered that the addition of a water-soluble organic amine to a stream in a hydroformylation process will generate a separate phase upon heating in the presence of syngas, wherein the separate phase contains a substantial portion of the rhodium from the stream. The generation of this rhodium-rich phase allows facile decantation of the undesirable aldehyde heavies along with simple recycle and recovery of the contained rhodium back to the hydroformylation process. Such an approach can advantageously increase the catalyst life and economics of hydroformylation processes and in particular, higher olfin hydroformylation processes.

In one aspect, the present invention relates to process to recover rhodium from a hydroformylation process, wherein the hydroformylation process comprises producing at least one aldehyde in a reaction zone, the reaction zone comprising a $C_7$ to $C_{22}$ olefin, hydrogen and carbon monoxide in the presence of a catalyst, wherein the catalyst comprises rhodium and an organophosphorus ligand. In some embodiments, a process of the present invention comprises (a) treating a catalyst-containing stream from the hydroformylation process with 2.5 to 20 weight percent, based on the total weight of the stream, of a water-soluble organic amine of the following structure:

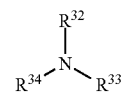

wherein $R^{32}$, $R^{33}$, and $R^{34}$ are each independently alkyls and ethoxylates, and wherein no more than one of $R^{32}$, $R^{33}$, and $R^{34}$ is alkyl; (b) heating the resulting solution in the presence of syngas to a temperature of at least 65° C. to generate a rhodium-rich phase and a supernatant; and (c) removing the supernatant to recover the rhodium-rich phase. In some embodiments, the ligand is an organomonophosphite.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an acid removal system such as an extractor or other immiscible fluid contacting system, (g) a treated or untreated fluid returned to a reaction zone or separation zone, (h) a fluid in an external cooler, and (i) ligand decomposition products and components derived from them, such as oxides, sulfides, salts, oligomers, and the like.

As used herein, "organomonophosphite ligands" are compounds containing a single phosphorous atom bound to three oxygen atoms; the three oxygen atoms are each additionally bound to carbon moieties. Illustrative examples include, but are not limited to monoorganophosphite, diorganophosphite, and triorganophosphite compounds, examples of which include: tris(2,4-di-t-butylphenyl)phosphite, 4,8-di-tert-butyl-6-(2-(tert-butyl)-4-methoxyphenyl)-2,10-dimethoxydibenzo[d,f][1,3,2]dioxaphosphepine, and the like.

The term "free ligand" means ligand that is not complexed with (or bound to) the metal, e.g., metal atom, of the complex catalyst.

As used herein, the terms "heavy byproducts" and "heavies" are used interchangeably and refer to byproducts that have a normal boiling point that is at least 25° C. above the normal boiling point of the desired product of the hydroformylation process. Such materials are known to form inherently in hydroformylation processes under normal operation through one or more side reactions, including for example, by aldol condensation or ligand degradation.

As used herein, the term "dimer" refers to heavy byproducts derived from two molecules of aldehyde. Likewise the term "trimer" refers to heavy byproducts derived from three molecules of aldehyde.

As used herein, the terms "separation zone" and "vaporizer" are used interchangeably and refer to a separation device wherein the product aldehyde is volatilized overhead, condensed and collected, while the non-volatile concentrated effluent (tails, or vaporizer tails) containing the homogeneous catalyst is returned to one or more of the reactors. The separation zone temperature is higher than the reactor temperature, and may optionally be operated at reduced pressure. In one embodiment, the vaporizer features flowing gas of varying composition that aids in product removal and optionally helps stabilize the catalyst ("strip gas vaporizer").

As used herein, the terms "feed to tails" and "feed to tails ratio" are used interchangeably and refer to the mass of reaction fluid entering the separation zone relative to the mass of vaporizer tails leaving the bottom of the separation zone and returning to the hydroformylation reactors. "Feed to tails" is an indicator of the rate at which volatiles, such as aldehyde product, are removed from the reaction fluid. For example, a "feed to tails ratio" of 2, means that the weight of reaction fluid entering the separation zone is two times greater than the weight of the concentrated effluent returned to the hydroformylation reactors.

As used herein, the term "liquid purge stream" means a liquid stream in a hydroformylation process that is leaving a recycle process used to remove an accumulation of inerts and unwanted materials that might otherwise build up.

Some embodiments of the present invention relate to processes for the recovery of rhodium in a hydroformylation process. Such rhodium recovery processes are particularly useful in hydroformylation processes that comprise producing at least one aldehyde in a reaction zone, the reaction zone comprising a $C_7$ to $C_{22}$ olefin, hydrogen, and carbon monoxide in the presence of a catalyst, wherein the catalyst comprises rhodium and an organophosphorus ligand. In some embodiments, processes for the recovery of rhodium in such a hydroformylation process comprise (a) treating a catalyst-containing stream from the hydroformylation process with 2.5 to 20 weight percent, based on the total weight of the stream, of a water-soluble organic amine of the following structure:

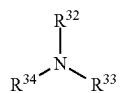

wherein $R^{32}$, $R^{33}$, and $R^{34}$ are each independently alkyls and ethoxylates, and wherein no more than one of $R^{32}$, $R^{33}$, and $R^{34}$ is alkyl; (b) heating the resulting solution in the presence of syngas to a temperature of at least 65° C. to generate a rhodium-rich phase and a supernatant; and (c) removing the supernatant to recover the rhodium-rich phase. In some embodiments, $R^{32}$, $R^{33}$, and $R^{34}$ are each ethoxylates. The organic amine, in some embodiments, is triethanolamine. In some embodiments, the syngas is provided in step (b) at atmospheric pressure or higher.

In some embodiments, the ligand is an organomonophosphite.

In some embodiments, processes of the present invention further comprise returning the rhodium-rich phase to the reaction zone. The rhodium is separated from the rhodium-rich phase in some embodiments. The rhodium is separated from the rhodium-rich phase, in some embodiments, by acidifying the rhodium-rich phase to a pH less than 6 in the presence of water and a water-immiscible organic solvent (e.g., any of the organic solvents described herein that are not water miscible), and optionally in the presence of an organophosphorus ligand, and returning the rhodium-containing organic solvent to the reaction zone. In some embodiments, an organic solvent (as described herein) is added to the rhodium-rich phase prior to returning the rhodium-rich phase to the reaction zone. In some embodiments, the rhodium-rich phase is treated with an organic solvent (as described herein), and the treated rhodium-rich phase is returned to the reaction zone.

In some embodiments, the catalyst-containing stream that is treated with the water-soluble organic amine is a liquid purge stream from the hydroformylation process.

In some embodiments, at least 50 weight percent of the rhodium from the catalyst-containing stream is present in the rhodium-rich phase.

In some embodiments, the supernatant from step (c) is treated with 2.5 to 20 weight percent of the water-soluble organic amine, and the treated supernatant is then heated in the presence of syngas to a temperature of at least 65° C. to generate a second rhodium-rich phase and a second supernatant. The second rhodium-rich phase is returned to the reaction zone in some embodiments. In some embodiments, rhodium is separated from the second rhodium-rich phase. The rhodium is separated from the second rhodium-rich phase, in some embodiments, by acidifying the rhodium-rich phase to a pH less than 6 in the presence of water and a water-immiscible organic solvent (e.g., any of the organic solvents described herein that are not water miscible), and optionally in the presence of an organophosphorus ligand, and returning the rhodium-containing organic solvent to the reaction zone.

Hydrogen and carbon monoxide are required for the process. These may be obtained from any suitable source, including petroleum cracking and refinery operations. Syngas mixtures are commonly used as a source of hydrogen and CO.

As used herein, "syngas" (from synthesis gas) refers to a gas mixture that contains varying amounts of CO and $H_2$. Production methods are well known and include, for example: (1) steam reforming and partial oxidation of natural gas or liquid hydrocarbons, and (2) the gasification of coal and/or biomass. Hydrogen and CO typically are the main components of syngas, but syngas may contain carbon dioxide and inert gases such as $CH_4$, $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The olefin starting material reactants that may be employed in the hydroformylation process of this invention include both optically active (prochiral and chiral) and non-optically active (achiral) olefinic unsaturated compounds containing from 7 to 22, preferably 8 to 20, carbon atoms. Such olefinic unsaturated compounds can be substituted or unsubstituted, terminally or internally unsaturated, straight-chain, branched chain or cyclic. Olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403) can be employed. Moreover, such olefin compounds may further contain one or more additional ethylenic unsaturated groups, and mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and such commercial olefins need not necessarily be purified from same prior to being hydroformylated. Illustrative mixtures of olefinic starting materials that can be employed in the hydroformylation reactions include, for example, mixed butene dimers and trimers. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809, 4,769,498 and the like.

Embodiments of the present invention are especially useful for the production of non-optically active aldehydes, by hydroformylating achiral alpha-olefins containing from 7 to 22, preferably 8 to 20, carbon atoms, and achiral internal olefins containing from 7 to 20 carbon atoms as well as starting material mixtures of such alpha olefins and internal olefins.

Illustrative alpha and internal olefins include, for example, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-heptene, 2-octene, propylene dimers, propylene trimers, propylene tetramers, 2-ethyl-1-hexene, and the like including mixtures thereof.

A solvent advantageously is employed in the hydroformylation process as well as, in some embodiments, separation of rhodium from a rhodium-rich phase. Any suitable solvent that does not unduly interfere with the hydroformylation process can be used. By way of illustration, suitable solvents for rhodium catalyzed hydroformylation include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, polyethers, alkylated polyethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In rhodium catalyzed hydroformylation, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. Indeed, while one may employ, if desired, any suitable solvent at the start-up of a continuous process, the primary solvent will normally eventually comprise both aldehyde products and higher boiling aldehyde liquid condensation by-products (heavies), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

Catalysts useful in hydroformylation processes comprise a catalytic metal. The catalytic metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium. Embodiments of the present invention are particularly well-suited for the recovery of rhodium such that in some embodiments, the catalytic metal is rhodium.

The number of available coordination sites on such metals is well known in the art. Thus the catalytic species, which may comprise a complex catalyst mixture, may comprise monomeric, dimeric or higher nuclearity forms, which are preferably characterized by at least one organophosphite-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphite ligands in view of the carbon monoxide and hydrogen gas employed by the hydroformylation reaction.

The catalysts, as well as methods for their preparation, are well known in the art and include those disclosed in the above-mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal.

The permissible organophosphorous ligands that make up the metal-organophosphorous ligand complexes and free organophosphorous ligand include mono-, di-, and triorganophosphites. Mixtures of such ligands may be employed if desired in the metal-organophosphorous ligand complex catalyst and/or free ligand and such mixtures may be the same or different. This invention is not intended to be limited in any manner by the permissible organomonophosphite ligands or mixtures thereof. It is to be noted that the successful practice of this invention does not depend and is not predicated on the exact structure of the metal-organomonophosphite ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organophosphorous ligand and carbon monoxide and/or hydrogen.

The term "complex" as used herein means a coordination compound formed by the union of one or more electronically rich molecules or atoms capable of independent existence with one or more electronically poor molecules or atoms, each of which is also capable of independent existence. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. The complex species are preferably free of any additional organic ligand or anion that might poison the catalyst or have an undue adverse effect on catalyst performance. It is preferred in the metal-organophosphite ligand complex catalyzed hydroformylation reactions that the active catalysts be free of halogen and sulfur directly bonded to the metal, although such may not be absolutely necessary.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, and triorganophosphite. Such organophosphorous ligands and/or methods for their preparation are well known in the art.

Representative monoorganophosphites may include those having the formula:

≪I≫ wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

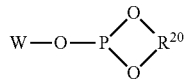  <<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 36 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, and 4,835,299, and PCT Publication WO2016087301, and the like.

Representative of a more preferred class of diorganophosphites are those of the formula:

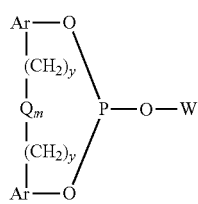  <<III>> wherein W is as defined above, each Ar is the same or different and represents a substituted or unsubstituted aryl radical, each y is the same or different and is a value of 0 or 1, Q represents a divalent bridging group selected from —$C(R^{35})_2$—, —O—, —S—, —$NR^{36}$—, $Si(R^{37})_2$ and —CO—, wherein each $R^{35}$ is the same or different and represents hydrogen, an alkyl radical having from 1 to 12 carbon atoms, phenyl, tolyl, and anisyl, $R^{36}$ is as defined above, each $R^{37}$ is the same or different and represents hydrogen or a methyl radical, and m has a value of 0 or 1. Such diorganophosphites are described in greater detail, for example, in U.S. Pat. Nos. 4,599,206, 4,717,775, and 4,835, 299, and PCT Publication WO2016087301.

Representative triorganophosphites may include those having the formula:

  <<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. The most preferred triorganophosphite is tris(2,4-di-t-butylphenyl)phosphite. Such triorganophosphites are described in greater detail, for example, in U.S. Pat. Nos. 3,527,809 and 4,717,775 and US Publication No. US20150336093.

If desired, make-up or additional organophosphorous ligand can be supplied to the reaction medium of the hydroformylation process at any time and in any suitable manner, e.g. to maintain a predetermined level of free ligand in the reaction medium.

The use of an aqueous buffer solution to prevent and/or lessen hydrolytic degradation of an organophosphite ligand and deactivation of a metal-organophosphite ligand complex is disclosed in U.S. Pat. No. 5,741,942. Aqueous buffers used in U.S. Pat. No. 5,741,944 are generally salts of weak acids or bases but are usually Group 1 or 2 metal (Na, K, Ca, etc.) salts of weak acids. In some cases where amines are used, they generate ionic salts, such as ammonium salts, when they neutralize and remove at least some amount of the phosphorus acidic compounds from the reaction fluid. The aqueous buffer solutions employable in this invention may comprise any suitable buffer mixture containing salts of oxyacids, the nature and proportions of which in the mixture are such that the pH of their aqueous solutions may range from 3 to 9, preferably from 4 to 8 and more preferably from 4.5 to 7.5. In this context suitable buffer systems may include mixtures of anions selected from the group consisting of phosphate, carbonate, citrate, maleate, fumarate, and borate compounds and cations selected from the group consisting of ammonium and alkali metals, e.g. sodium, potassium and the like. Such buffer systems and/or methods for their preparation are well known in the art. The use of a buffer extractor particularly in the stream with the recovered rhodium to remove acids or other impurities prior to being introduced back into the reaction system is preferred.

The hydroformylation products may be asymmetric, non-asymmetric or a combination thereof, with the preferred products being non-asymmetric. The process may be conducted in any batch, continuous or semi-continuous fashion and may involve any catalyst liquid and/or gas recycle operation desired.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e., vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In one embodiment, the hydroformylation reaction fluid employable herein includes any fluid derived from any corresponding hydroformylation process that contains the organic amine and at least some amount of four different main ingredients or components, i.e., the aldehyde product, a metal-organophosphorous ligand complex catalyst, free organophosphorous ligand and an organic solubilizing agent for said catalyst and said free ligand, said ingredients corresponding to those employed and/or produced by the hydroformylation process from whence the hydroformylation reaction mixture starting material may be derived. The hydroformylation reaction mixture compositions employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process encompassed by this invention may include any suitable hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformylation process of this invention is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide in a reaction zone may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature from $-25°$ C. to $200°$ C. In general, hydroformylation reaction temperatures of $50°$ C. to $120°$ C. are preferred for all types of olefinic starting materials. It is to be understood that when non-optically active aldehyde products are desired, achiral type olefin starting materials and organophosphorous ligands are employed and when optically active aldehyde products are desired prochiral or chiral type olefin starting materials and organophosphorous ligands are employed. The hydroformylation reaction conditions employed will be governed by the type of aldehyde product desired.

The hydroformylation process of this invention may be carried out using one or more suitable reactors such as, for example, a fixed bed reactor, a fluid bed reactor, a tubular reactor, a venturi reactor, a bubble column reactor, a continuous stirred tank reactor (CSTR) or a slurry reactor. The optimum size and shape of the reactor will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. As discussed further below, hydroformylation processes can comprise one more reaction zones, one or more separation zones, and one or more buffer treatment zones. The reaction zone(s) employed in this invention may be a single vessel or may comprise two or more discrete vessels. The separation zone(s) employed in this invention may be a single vessel or may comprise two or more discrete vessels. The buffer treatment zone(s) employed in this invention may be a single vessel or may comprise two or more discreet vessels. The reaction zone(s) and separation zone(s) employed herein may exist in the same vessel or in different vessels. For example, reactive separation techniques such as reactive distillation, reactive membrane separation and the like may occur in the reaction zone(s).

The hydroformylation process of this invention can be conducted in a batch or continuous fashion, with recycle of unconsumed starting materials if required. The hydroformylation reaction can be conducted in a single reaction zone or in a plurality of reaction zones, in series or in parallel or it may be conducted batchwise or continuously in an elongated tubular zone or series of such reaction zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the process especially to maintain the desired molar ratio of the starting materials. The reaction steps may be effected by the incremental addition of one of the starting materials to the other. Also, the reaction steps can be combined by the joint addition of the starting materials. The starting materials may be added to each or all the reaction zones in series. When complete conversion is not desired or not obtainable, the starting materials can be separated from the product, for example by distillation, and the starting materials then recycled back into the reaction zone.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

As indicated above, it is generally preferred to carry out the hydroformylation process of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation, phase separation, filtration and the like or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation. Such membrane separation can be achieved as set out in U.S. Pat. Nos. 5,430,194 and 5,681,473.

As indicated above, at the conclusion of (or during) the process of this invention, the desired aldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture (commonly referred to as "vaporizer tails" when a vaporizer is used) may then be recycled back to the reactor as may, if desired, any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products. When an alpha-mono-olefin reactant is also employed, the aldehyde derivative thereof can also be separated by the above methods.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

The present invention focuses on the recovery of rhodium from streams within the hydroformylation process. Some embodiments of the present invention are particularly useful in removing rhodium from a concentrated catalyst stream following a product (aldehyde)/catalyst separation zone. For example, when a vaporizer is used to separate the aldehyde product, some embodiments of the present invention can be used to remove rhodium from the vaporizer tails which is a concentrated catalyst stream.

According to embodiments of the present invention, the catalyst-containing stream is treated with a water-soluble organic amine of the following structure:

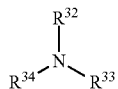

wherein $R^{32}$, $R^{33}$, and $R^{34}$ are each independently alkyls and ethoxylates, and wherein no more than one of $R^{32}$, $R^{33}$, and $R^{34}$ is alkyl. In some embodiments, to the extent one of $R^{32}$, $R^{33}$, and $R^{34}$ is an alkyl, the alkyl is either methyl or ethyl. For the purpose of this disclosure, an "ethoxylate" is a $(-CH_2-CH_2-O)_nH$ moiety wherein n is equal to 1 or 2. A particularly desirable water-soluble organic amine for use in embodiments of the present invention is triethanolamine.

Advantageously, the water-soluble organic amine has the following two properties: 1) it is weakly basic in order to avoid heavies formation in the reaction zone; and 2) it is water-soluble to avoid accumulation in the reaction fluid. The alkalinity or basicity of the water-soluble organic amine is generally reported as the pKa of the conjugate acid, which advantageously is from 5 to 11 at the temperature of the extraction zone. The pKa is from 6.0 to 9.5 in some embodiments, and is from 6.5 to 9.0 in some particularly desirable embodiments. Candidates for the organic amine can be tested for heavies formation by heating the product aldehyde with the organic amine at elevated temperature. Acceptable organic amines will exhibit less than 1 gram of heavies formation per liter of test solution per day at hydroformylation temperatures. The amount of heavies formation can be readily determined by gas or liquid chromatography, as is known to those skilled in the art. The minimum water solubility is at least 5% soluble in water at 25° C. and preferably miscible with water at 25° C. and higher.

The water-soluble organic amine is employed in an amount sufficient to generate a separate phase when heated under syngas. Mixtures of organic amines can be employed. In some embodiments, the water-soluble organic amine is employed in an amount to provide 2.5 to 20 weight percent of the organic amine in the catalyst-containing stream, based on the total weight of the catalyst-containing stream. The water-soluble organic amine is employed, in some embodiments, in an amount to provide 2.5 to 10 weight percent of the organic amine in the catalyst-containing stream, based on the total weight of the catalyst-containing stream. In some embodiments, the water-soluble organic amine is employed in an amount to provide 2.5 to 5 weight percent of the organic amine in the catalyst-containing stream, based on the total weight of the catalyst-containing stream. The concentration of the organic amine in the reaction fluid in the reaction zone can be measured by conventional techniques well-known to those skilled in the art including, for example, gas chromatography and liquid chromatography.

The catalyst-containing stream with the water-soluble organic amine is heated under syngas to a temperature of at least 65° C. In some embodiments, the catalyst-containing stream with the water-soluble organic amine is heated under syngas to a temperature of at least 70° C., or to at least 75° C., or to at least 80° C., or to at least 85° C., or to at least 90° C. In general, the catalyst-containing stream with the water-soluble organic amine should be heated to a temperature that does not exceed the boiling point of the product aldehyde. In some embodiments, the syngas pressure is one atmosphere or more. In some embodiments, the syngas pressure is at or about one atmosphere. By heating the catalyst-containing stream under syngas, a separate, bottom phase is obtained, generally a colored viscous material which contains most of the rhodium originally in the catalyst-containing stream. The top organic phase, or supernatant, is removed and may optionally be processed elsewhere such as by wiped film evaporator (WFE) or other means to recover product aldehyde or by other techniques to recover any further residual rhodium. In some embodiments, the supernatant can again be treated with 2.5 to 20 weight percent of the water-soluble organic amine, and then heated in the presence of syngas to a temperature of at least 65° C. to generate a second rhodium-rich phase and a second supernatant. In such embodiments, the second rhodium-rich phase can be returned to the reaction zone like the first rhodium-rich phase as discussed below. In some further embodiments, an organic solvent can be added to the second rhodium-rich phase prior to returning the second rhodium-rich phase to the reaction zone.

The rhodium contained in the bottom layer may then be returned to the reaction zone by extraction with a suitable organic solvent as described above, preferably the product aldehyde, which also preferably contains additional organophosphorus ligand. Alternatively, the rhodium-rich bottom layer may be acidified (preferably to pH less than 6 and most preferably less than 3) in the presence of water and a water-immiscible organic solvent (e.g., the product aldehyde) and preferably containing additional ligand, and then the rhodium-containing organic solvent can be returned to the reaction zone.

The additional ligand that can be added during separation of rhodium from the rhodium-rich layer may be the same or different than the hydroformylation reaction system from which the catalyst solution was obtained but it should not be an inhibitor to the catalyst system into which the resulting rhodium complex will be sent. The amount of additional ligand is not critical but should be at least 5 moles of ligand per mole of rhodium atoms, preferably greater than 10 and most preferably more than 20.

Residual water soluble organic amines as described herein may be present in the stream being returned to the process and optionally can be removed by an aqueous extractor that may already be in place to control system acidity as described in U.S. Pat. Nos. 5,741,942 and 5,741,944. Alternatively, batchwise or periodic water washing of the catalyst fluid or portions thereof can be performed to remove the water soluble organic amines and other polar contaminants. In some embodiments, the treated stream is washed with water or aqueous buffer prior to it being introduced back into the reaction system.

Accordingly, illustrative non-optically active aldehyde products include e.g., octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, and the like.

Some embodiments of the invention will now be described in more detail in the following Examples.

EXAMPLES

All parts and percentages in the following examples are by weight unless otherwise indicated. Pressures are given as absolute pressure unless otherwise indicated. The mixed $C_4$, $C_5$, and $C_9$ aldehydes were obtained from a process for the hydroformylation of mixed octenes, and were distilled prior to use unless otherwise noted. 2-ethylhexanal was purchased from TCI America and used without further purification.

Rhodium concentration is determined by atomic absorption (AA) using an air/acetylene flame. It has been found that this technique will not reliably quantify clustered rhodium; thus, this method may be used to indicate "rhodium loss" (e.g., undetectable rhodium is clustered or otherwise no longer in solution). Color change (starting from a colorless or light yellow solution), such as darkening or formation of black film or solids is also indicative of rhodium catalyst degradation.

Ligand A is tris(2,4-di-tert-butylphenyl) phosphite:

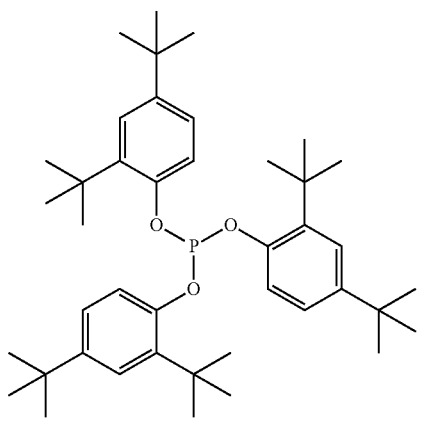

Ligand A

In the following Examples, a catalyst-containing solution (Catalyst Solution A) is used. Catalyst Solution A is an isononyl aldehyde-derived hydroformylation catalyst solution containing 172 ppmw of rhodium, 2.1 weight percent of Ligand A, 19 weight percent heavies, and 11 weight percent $C_8$ olefins, with the balance being isononyl aldehydes.

Inventive Example 1: 18.0 g of Catalyst Solution A is mixed with 1.2 g TEA and the resulting solution (6.3 wt % TEA) is sparged with 1:1 $H_2$:CO for 2 minutes at ambient temperature and pressure. The syngas-treated catalyst solution is next stirred at 90° C. for 3 hours. During this time, a dark brown mixture phase separates from the bulk catalyst solution. The phase-separated catalyst solution is allowed to cool and settle for 10 minutes, and a sample is withdrawn from the supernatant for Rh atomic absorption analysis. The supernatant rhodium concentration is reduced from 162 ppmw rhodium to 76 ppmw, indicating that 54% of the soluble rhodium has been captured in the phase-separated mixture.

Inventive Example 2: 18.0 g of Catalyst Solution A is mixed with 1.2 g TEA and the resulting solution (6.3 wt % TEA) is sparged with 1:1 $H_2$:CO for 2 minutes at ambient temperature and pressure. The syngas-treated catalyst solution is next stirred at 70° C. for 3 hours. During this time, a dark brown mixture phase separates from the bulk catalyst solution. The phase-separated catalyst solution is allowed to cool and settle for 10 minutes and a sample is withdrawn from the supernatant for Rh atomic absorption analysis. The supernatant rhodium concentration is reduced from 162 ppmw rhodium to 84 ppmw, indicating that 48% of the soluble rhodium has been captured in the phase-separated mixture.

Comparative Experiment A: 18.0 g of Catalyst Solution A is mixed with 1.2 g TEA and the resulting solution (6.3 wt % TEA) is sparged with 1:1 $H_2$:CO for 2 minutes at ambient temperature and pressure. The syngas-treated catalyst solution is next stirred at 50° C. for 3 hours. During this time, no phase separation is observed. After 24 hours at 50° C., although a small amount of a brown precipitate has collected on the sides of the glass bottle, no phase separation of a dark brown mixture has occurred.

Comparative Experiment B: 18.0 g of Catalyst Solution A is mixed with 1.2 g TEA and the resulting solution (6.3 wt % TEA) is stirred at 90° C. for 20 hours. No syngas treatment preceded the heat treatment. During this time, the catalyst solution does not change color and no phase separation is observed.

Comparative Experiment C: 18.0 g of Catalyst Solution A is mixed with 1.2 g triisopropanolamine and the resulting solution (6.3 wt % triisopropanolamine) is sparged with 1:1 $H_2$:CO for 2 minutes at ambient temperature and pressure. The syngas-treated catalyst solution is next stirred at 90° C. for 3 hours. During this time, the catalyst solution develops a brown color, but phase separation is not observed.

Comparative Experiment D: 18.0 g of Catalyst Solution A is mixed with 1.2 g triethylamine and the resulting solution (6.3 wt % triethylamine) is sparged with 1:1 $H_2$:CO for 2 minutes at ambient temperature and pressure. The syngas-treated catalyst solution is next stirred at 90° C. for 3 hours. During this time, the catalyst solution develops a brown color, but phase separation is not observed.

Comparative Experiment E: 18.0 g of Catalyst Solution A is mixed with 1.2 g PRIMENE™ TOA (t-octylamine) and the resulting solution (6.3 wt % PRIMENE™ TOA) is sparged with 1:1 $H_2$:CO for 2 minutes at ambient temperature and pressure. The syngas-treated catalyst solution is next stirred at 90° C. for 3 hours. During this time, the catalyst solution does not change color and no phase separation is observed.

The results of Inventive Examples 1-2 and Comparative Experiments A-E are summarized in Table 1.

TABLE 1

| | Catalyst Solution | Syngas Pre-Treatment (Y or N) | Temp. (° C.) | Amine (wt %) | Phase Separation of Rh-Rich Phase (Y or N) |
|---|---|---|---|---|---|
| Inv. Ex. 1 | A | Y | 90 | Triethanolamine (6.3) | Y |
| Inv. Ex. 2 | A | Y | 70 | Triethanolamine (6.3) | Y |
| Comp. Ex. A | A | Y | 50 | Triethanolamine (6.3) | N |
| Comp. Ex. B | A | N | 90 | Triethanolamine (6.3) | N |
| Comp. Ex. C | A | Y | 90 | Triisopropanolamine (6.3) | N |

TABLE 1-continued

| | Catalyst Solution | Syngas Pre-Treatment (Y or N) | Temp. (° C.) | Amine (wt %) | Phase Separation of Rh-Rich Phase (Y or N) |
|---|---|---|---|---|---|
| Comp. Ex. D | A | Y | 90 | Triethylamine (6.3) | N |
| Comp. Ex. E | A | Y | 90 | t-Octylamine (6.3) | N |

As shown in Table 1, syngas and triethanolamine (6.2 wt %) treatment induce phase separation of a rhodium-rich phase from an isononyl aldehyde-derived hydroformylation catalyst modified by Ligand A. Heating the catalyst solution at temperatures ≥70° C. is sufficient to induce phase separation within 3 hours, while heating at 50° C. is ineffective after 24 hours.

Inventive Example 3: 19.5 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 271 ppmw of rhodium, 1.5 wt % Ligand A, and 6.2 wt % triethanolamine. This catalyst solution is sparged with 1:1 $H_2$:CO for 2 minutes at ambient temperature and pressure and thereafter stirred at 90° C. for 3 hours. During this time, a dark brown mixture phase-separates from the bulk catalyst solution. The supernatant rhodium concentration is reduced from 271 ppmw rhodium to 76 ppmw, indicating that 72% of the soluble rhodium has been captured in the phase-separated mixture.

Inventive Example 4: 19.5 g of a synthetic 2-ethylhexanal-derived hydroformylation catalyst-containing solution is prepared and contains 92 wt % 2-ethylhexanal, 237 ppmw rhodium, 1.5 wt % Ligand A and 6.2 wt % triethanolamine. This catalyst solution is sparged with 1:1 $H_2$:CO for 2 minutes at ambient temperature and pressure and thereafter stirred at 90° C. for 3 hours. During this time, a dark brown mixture phase-separates from the bulk catalyst solution. The supernatant rhodium concentration is reduced from 237 ppmw rhodium to 70 ppmw, indicating that 71% of the soluble rhodium has been captured in the phase-separated mixture.

Inventive Example 5: 19.5 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 252 ppmw of rhodium, 1.5 wt % Ligand A, and 6.2 wt % methyldiethanolamine. This catalyst solution is sparged with 1:1 $H_2$:CO for 2 minutes at ambient temperature and pressure and thereafter stirred at 90° C. for 3 hours. During this time, a dark brown mixture phase-separates from the bulk catalyst solution. The supernatant rhodium concentration is reduced from 252 ppmw rhodium to 187 ppmw, indicating that 26% of the soluble rhodium has been captured in the phase-separated mixture.

Inventive Example 6: 19.6 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 277 ppmw of rhodium, 1.5 wt % Ligand A, 6.2 wt % methyldiethanolamine, and 0.5 wt % deionized water. This catalyst solution is sparged with 1:1 $H_2$:CO for 2 minutes at ambient temperature and pressure and thereafter stirred at 90° C. for 3 hours. During this time, a dark brown mixture phase-separates from the bulk catalyst solution. The supernatant rhodium concentration is reduced from 277 ppmw rhodium to 193 ppmw, indicating that 30% of the soluble rhodium has been captured in the phase-separated mixture.

Comparative Example F: 19.5 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 268 ppmw of rhodium, 1.5 wt % Ligand A, and 6.2 wt % triisopropanolamine. This catalyst solution is sparged with 1:1 $H_2$:CO for 2 minutes at ambient temperature and pressure and thereafter stirred at 90° C. for 3 hours. During this time, no phase separation of a rhodium-rich phase is observed.

Comparative Example G: 19.6 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 271 ppmw of rhodium, 1.5 wt % Ligand A, 6.2 wt % triisopropanolamine, and 0.5 wt % deionized water. This catalyst solution is sparged with 1:1 $H_2$:CO for 2 minutes at ambient temperature and pressure and thereafter stirred at 90° C. for 3 hours. During this time, no phase separation of a rhodium-rich phase is observed.

Comparative Example H: 19.5 g of a butyraldehyde-derived hydroformylation catalyst-containing solution is prepared and contains 92 wt % butyraldehydes/heavies (41 wt % butyraldehyde, 59 wt % heavies), 85 ppmw Rh, and 1.5 wt % Ligand A, and 6.2 wt % triethanolamine. This catalyst solution is sparged with 1:1 $H_2$:CO for 2 minutes at ambient temperature and pressure and thereafter stirred at 90° C. for 3 hours. During this time, no phase separation of a rhodium-rich phase is observed.

Comparative Example I: 19.6 g of a valeraldehyde-derived hydroformylation catalyst-containing solution is prepared and contains 92 wt % valeraldehydes/heavies (97 wt % valeraldehyde, 3 wt % heavies), 160 ppmw rhodium, 2.0 wt % Ligand A, and 6.1 wt % triethanolamine. This catalyst solution is sparged with 1:1 $H_2$:CO for 2 minutes at ambient temperature and pressure and thereafter stirred at 90° C. for 3 hours. During this time, no phase separation of a rhodium-rich phase is observed.

The results of Inventive Examples 3-6 and Comparative Examples F-I are summarized in Table 2.

TABLE 2

| | Catalyst Solution | Aldehyde Heavies Concentration (wt %) | Amine (wt %) | Phase Separation of Rh-Rich Phase (Y or N) |
|---|---|---|---|---|
| Inv. Ex. 3 | C9 | 3 | Triethanolamine (6.2) | Y |
| Inv. Ex. 4 | C8 | 0 | Triethanolamine (6.2) | Y |
| Inv. Ex. 5 | C9 | 3 | Methyldiethanolamine (6.2) | Y |
| Inv. Ex. 6 | C9 | 3 | Methyldiethanolamine (6.2)* | Y |
| Comp. Ex. F | C9 | 3 | Triisopropanolamine (6.2) | N |
| Comp. Ex. G | C9 | 3 | Triisopropanolamine (6.2)* | N |
| Comp. Ex. H | C4 | 59 | Triethanolamine (6.2) | N |
| Comp. Ex. I | C5 | 3 | Triethanolamine (6.2) | N |

*0.5 weight percent of water is added with the amine

As shown in Table 2, the syngas and triethanolamine treatment is only effective at inducing phase separation of a rhodium-rich phase with the C8 and C9 aldehyde-derived hydroformylation catalyst solutions. Also, triisopropanolamine is ineffective, in the presence or absence of 0.5 wt % deionized water.

Inventive Example 7: 19.5 g of a synthetic isononyl aldehyde-derived hydroformylation catalyst-containing solution is prepared and contains 92 wt % isononyl aldehydes/heavies (97 wt % isononyl aldehydes, 3 wt % isononyl aldehyde heavies), 262 ppmw rhodium, 1.5 wt % triphenylphosphite, and 6.2 wt % triethanolamine. This catalyst solution is sparged with 1:1 $H_2$:CO for 2 minutes at ambient temperature and pressure and thereafter stirred at 90° C. for 3 hours. During this time, a dark brown mixture phase-separates from the bulk catalyst solution. The supernatant rhodium concentration is reduced from 262 ppmw rhodium to 24 ppmw, indicating that 91% of the soluble rhodium has been captured in the phase-separated mixture.

Comparative Example J: 19.5 g of a synthetic isononyl aldehyde-derived hydroformylation catalyst is prepared and contains 92 wt % isononyl aldehydes/heavies (77 wt % isononyl aldehydes, 20 wt % octenes, 3 wt % isononyl aldehyde heavies), 160 ppmw rhodium, 0.38 wt % 6,6'-[[3,3',5,5'-tetrakis(1,1-dimethylethyl)-[1,1'-biphenyl]-2,2'-diyl]bis(oxy)]bisdibenzo[d,f][1,3,2]-dioxaphosphepin ("Ligand B"), and 6.2 wt % triethanolamine. This catalyst solution is sparged with 1:1 $H_2$:CO for 2 minutes at ambient temperature and pressure and thereafter stirred at 90° C. for 3 hours. During this time, no phase separation of a dark brown, rhodium-rich phase is observed.

Comparative Example K: 21.0 of a synthetic isononyl aldehyde-derived hydroformylation catalyst is prepared and contains 86 wt % aldehydes/heavies (97 wt % isononyl aldehydes, 3 wt % isononyl aldehyde heavies), 219 ppmw rhodium, 8.6 wt % triphenylphosphine, and 5.7 wt % triethanolamine. This catalyst solution is sparged with 1:1 $H_2$:CO for 2 minutes at ambient temperature and pressure and thereafter stirred at 90° C. for 3 hours. During this time, no phase separation of a dark brown, rhodium-rich phase is observed.

The results of Inventive Example 7 and Comparative Examples J-K are summarized in Table 3.

TABLE 3

| | Catalyst Solution | Organophosphorous Ligand (wt %) | Amine (wt %) | Phase Separation of Rh-Rich Phase (Y or N) |
|---|---|---|---|---|
| Inv. Ex. 7 | C9 | Triphenylphosphite (1.5) | Triethanolamine (6.2) | Y |
| Comp. Ex. J | C9 | Ligand B (0.38) | Triethanolamine (6.2) | N |
| Comp. Ex. K | C9 | Triphenylphosphine (8.6) | Triethanolamine (5.7) | N |

As shown in Table 3, the syngas and triethanolamine treatment is effective with triphenylphosphite, but ineffective with either Ligand B or triphenylphosphine.

General Procedure for Hydroformylation Process

The catalyst-containing solution referenced in the Inventive Example below is prepared in a $N_2$-padded purge box and transferred via vacuum into a 100 mL Parr mini-reactor. The catalyst-containing solution is then preheated with agitation (500 rpm) to 70° C. under 1:1:1 gas (equal parts propylene:carbon monoxide:hydrogen) for 30 minutes. A pressure of approximately 50 psig 1:1:1 gas is established during this time with a Brooks model 5866 flow meter and after the 30 minute catalyst activation period, the reactor pressure is increased to 140 psig. The pressure is held constant for a run time of 1-2 hours and total gas uptake is measured with a Brooks 0151E totalizer. The hydroformylation rate (mol/L·hr) is calculated from the total gas uptake.

Inventive Example 6 (Batch Hydroformylation Test Using Recovered Rhodium):

The supernatant from Inventive Example 1 is removed from the phase-separated mixture and the dark brown, rhodium-rich phase is treated with 15.0 mL deionized water, followed by 20 mL 90/10 mixed $C_9$ aldehydes/$C_8$ olefins. The biphasic solution is mixed at ambient temperature and solid phosphorous acid is added until the pH of the aqueous phase is <2.0. The resulting acidified biphasic solution is mixed at ambient temperature and the organic phase is collected, treated with Ligand A (0.08 g), and tested for hydroformylation activity according to the General Procedure described above.

Inventive Example 7 (Batch Hydroformylation Test using Recovered Rhodium):

The supernatant from Inventive Example 3 is removed from the phase-separated mixture and the dark brown, rhodium-rich phase is treated with 1.0 mL deionized water and 19.0 mL tetrahydrofuran, sequentially; next, Ligand A (0.3 g) is added and the resulting solution is mixed and tested for hydroformylation activity according to the General Procedure described above.

The results of Inventive Examples 6 and 7 are summarized in Table 4.

TABLE 4

| | Recovery Procedure | Average Propylene Hydroformylation Rate (mol/L · hr) |
|---|---|---|
| Inv. Ex. 6 | Acidification, organic extraction | 1.42 |
| Inv. Ex. 7 | Aqueous THF extraction | 0.49 |

As shown in Table 4, both procedures for recovery of active rhodium from the rhodium-rich phase generate active hydroformylation catalysts.

What is claimed is:

1. A process to recover rhodium from a hydroformylation process that comprises producing at least one aldehyde in a reaction zone, the reaction zone comprising a $C_7$ to $C_{22}$ olefin, hydrogen and carbon monoxide in the presence of a catalyst, wherein the catalyst comprises rhodium and an organophosphorus ligand, wherein the process comprises:
    (a) treating a catalyst-containing stream from the hydroformylation process with 2.5 to 20 weight percent, based on the total weight of the stream, of a water-soluble organic amine of the following structure:

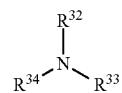

wherein $R^{32}$, $R^{33}$, and $R^{34}$ are each independently alkyls and ethoxylates, and wherein no more than one of $R^{32}$, $R^{33}$, and $R^{34}$ is alkyl;
    (b) heating the resulting solution in the presence of syngas to a temperature of at least 65° C. to generate a rhodium-rich phase and a supernatant; and (c) removing the supernatant to recover the rhodium-rich phase.

2. The process of claim 1, wherein the ligand is an organomonophosphite.

3. The process of claim 1, wherein $R^{32}$, $R^{33}$, and $R^{34}$ are each ethoxylates.

4. The process of claim 1, wherein the water-soluble organic amine is triethanolamine.

5. The process of claim 1, further comprising returning the rhodium-rich phase to the reaction zone.

6. The process of claim 1, further comprising treating the rhodium-rich phase with an organic solvent, and returning the treated rhodium-rich phase to the reaction zone.

7. The process of claim 1, further comprising separating the rhodium from the rhodium-rich phase by acidifying the rhodium-rich phase to a pH less than 6 in the presence of water and a water-immiscible organic solvent, and optionally in the presence of an organophosphorus ligand, and returning the rhodium-containing organic solvent to the reaction zone.

8. The process of claim 1, wherein the syngas is provided in step (b) at atmospheric pressure or higher.

9. The process of claim 1, wherein the catalyst-containing stream is a liquid purge stream from the hydroformylation process.

10. The process of claim 1, wherein at least 50 weight percent of the rhodium from the catalyst-containing stream is present in the rhodium-rich phase.

11. The process of claim 1, further comprising:
(d) treating the supernatant from step (c) with 2.5 to 20 weight percent of the water-soluble organic amine; and
(e) heating the treated supernatant in the presence of syngas to a temperature of at least 65° C. to generate a second rhodium-rich phase and a second supernatant.

* * * * *